United States Patent [19]
Collins et al.

[11] Patent Number: 4,902,224
[45] Date of Patent: Feb. 20, 1990

[54] CRYSTALLINE ORTHODONTIC BRACKET
[75] Inventors: Paul R. Collins, Washougal, Wash.; Larry R. Rothrock, Poway, Calif.
[73] Assignee: Union Carbide Chemicals and Plastics Company Inc., Danbury, Conn.
[21] Appl. No.: 286,168
[22] Filed: Dec. 19, 1988
[51] Int. Cl.⁴ .............................. A61C 7/00
[52] U.S. Cl. ............................................. 433/8
[58] Field of Search ............... 433/8, 9, 201.1, 202.1
[56] References Cited
U.S. PATENT DOCUMENTS 4,219,617 8/1980 Wallshein ............................. 433/8
4,595,598 6/1986 De Luca et al. ...................... 433/8
4,604,097 8/1986 Graves, Jr. et al. ............. 433/201.1
4,639,218 1/1987 Jones et al. ............................ 433/8
4,669,980 6/1987 Degnan ................................. 433/8
4,687,441 8/1987 Klepacki ............................... 433/8
4,789,649 12/1988 Abert et al. ..................... 433/201.1
4,799,882 1/1989 Kesling ................................. 433/8

Primary Examiner—Paul J. Hirsch
Attorney, Agent, or Firm—Morris N. Reinisch

[57] ABSTRACT

A crystalline orthodontic bracket with enhanced tolerance to fabrication, installation and use is composed of zirconia, yttria, magnesia or strontium titanate.

9 Claims, 3 Drawing Sheets

F I G. 2
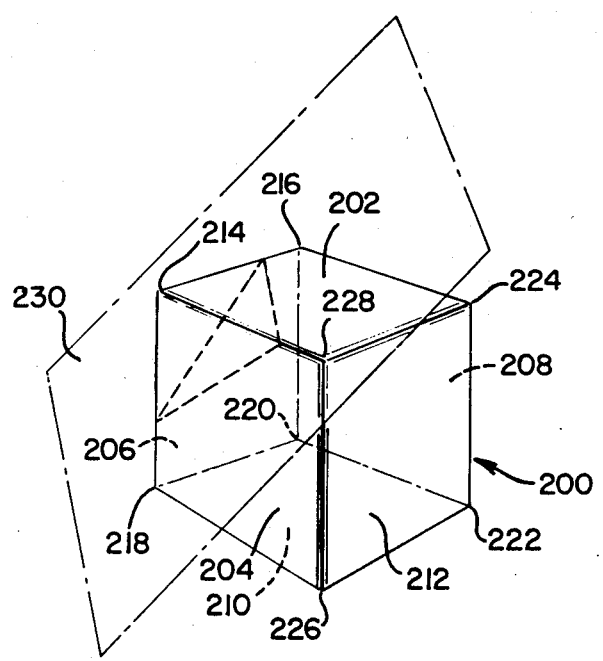

CRYSTALLINE ORTHODONTIC BRACKET

The invention relates to an orthodontic bracket having tie wings and a base and being composed of a crystalline zirconia, yttria, magnesia, titania or strontium titanate having a cubic crystalline structure.

BACKGROUND TO THE INVENTION

Orthodontic brackets attach directly to teeth and serve to transmit corrective forces from an orthodontic archwire to the tooth to which the bracket is attached. The requirements for an orthodontic bracket are quite severe. First, it must have sufficient mechanical strength to withstand the forces to which it will be subjected, including the forces transmitted by an archwire, ligation forces, and mastication forces. Second, it must be chemically inert in the oral environment so that it will not corrode and will be and remain biologically inert. The bracket must meet these requirements, and still remain small enough to fit on the tooth.

The overwhelming majority of orthodontic brackets in use today are made of metal, usually stainless steel. Metal brackets meet all of the essential requirements, but they have one undesirable attribute—they are unsightly. A person undergoing orthodontic treatment has a conspicuous amount of metal in full view on the front surfaces of his or her teeth. And since the treatment extends over a number of years, this unsightly appearance must be endured for a considerable period of time.

The incentive to make brackets from less unsightly materials has existed for many years. But recently, orthodontic treatment has been given to increasing numbers of adults, for whom the unsightly appearance of metal brackets is more than a mere annoyance. Ceramic brackets have been proposed but have a tendency to stain, especially if the bracket must be worn for extended periods of time. Therefore, the incentive to provide more esthetic orthodontic treatment is even greater now than it has ever been.

Recently, sapphire (crystalline alphaalumina) has found commercial application as the material of construction for orthodontic brackets. U.S. Pat. No. 4,639,218 discloses sapphire orthodontic brackets, and sapphire orthodontic brackets are currently manufactured and sold by "A" Company, Inc., a subsidiary of the Johnson & Johnson Company, and Ormco Corporation. While these brackets are esthetically pleasing, i.e., are transparent and do not stain, concerns exist about the durability of the brackets made from sapphire under the considerable stresses on the bracket induced by the arch wire, ligation and mastication. Sapphire is more subject to fracturing and chipping than metal. Not only is this property undesirable from the standpoint of its use as an orthodontic bracket, but also, fractures and chips occurring during the fabrication of the bracket result in loss in yield.

Sapphire is characterized as having a number of crystalline planes. These planes include the "a" plane, "c" plane, "m" plane, "n" plane and "r" plane. It is generally known that the crystal structure is weaker along the "r" plane than along the remaining crystal planes, which remaining planes have approximately the same strengths.

The sapphire orthodontic brackets that have been commercially available are believed by us to be made from "r" plane blanks and thus an "r"-plane would generally be parallel to the front face of the bracket or from EFG technique grown material in which the edge face was an "m" plane and the "c" plane extended substantially perpendicularly between the front and back faces parallel to the longitudinal axis of the arch wire groove. The cleavage of the tie wings at the arch wire groove and/or chipping of the corners of the tie wings, especially during fabrication, can occur due to these orientations of "r" planes.

One solution to these problems with sapphire orthodontic brackets involves the use of specific orientations of the sapphire within the bracket as disclosed in our copending U.S. Pat. application Ser. No. 220,303, filed July 18, 1988.

BRIEF SUMMARY OF THE INVENTION

By this invention, crystalline orthodontic brackets are provided that exhibit enhanced resistance to fracturing and chipping during fabrication, installation and use. These crystalline materials used in the orthodontic brackets of this invention exhibit desirable transparency and resistance to staining for use as orthodontic brackets and are chemically inert for use as orthodontic brackets. Advantageously, the crystalline materials are characterized as having a cubic crystalline structure in which each of the crystalline planes are relatively strong in comparison to the "r" planes of sapphire. Hence, the crystalline materials may exhibit excellent resistance to fracturing and chipping during fabrication of the bracket, its installation and its functioning within the mouth of the user. The transparent, crystalline materials having the cubic structure used in accordance with this invention are zirconia, yttria, magnesia and strontium titanate. Zirconia is the most preferred material. The high melting points of these materials lead to excellent room temperature strength. Though cleavage planes are present, the energy for cleavage is generally high and can be maximized by reducing the defect density during preparation. Published mechanical properties of these materials are limited and somewhat unreliable due to the (presently) limited methods of production. Since the strength of a crystal is directly related to its crystalline perfection, observed strength should increase as improved methods of production are developed.

Orthodontic brackets comprise a body having base face (the side intended to face the tooth); a front face on the side opposing the base face, the front face defining a longitudinal arch wire groove; upper and lower sides extending between the base face and front face and edge faces between which faces the arch wire groove extends. In accordance with a preferred embodiment of this invention, the orthodontic bracket is fabricated from crystalline stock in which the axis of each plane of the crystalline material is at an angle of between about 50° and 70° with respect to the longitudinal axis of the arch wire groove.

BRIEF DESCRIPTION OF THE DRAWINGS

FIG. 2 is a perspective view of intersecting planes in crystals having cubic structures;

DETAILED DESCRIPTION OF THE INVENTION

As used herein, the term "crystalline material" is intended to include only essentially monocrystalline material, that is, material comprised of a single crystal or two or more single crystals grown together longitudinally but separated by a relatively small angle (usually within 4°, determined with respect to the axes of neighboring single crystals) grain boundary. Most preferably, these grain boundaries do not vary by more than about 1°.

The crystalline material may solely consist of the material, i.e., zirconium and oxygen atoms in the case of zirconia, or may contain minor amounts of impurities or dopants, i.e., metal elements which become incorporated into the crystalline framework.

Crystalline stock can be produced by various techniques from the molten material. One technique is the EFG (for Edge defined, Film-fed, Growth) technique which is a modification of the Czochralski process for growing crystalline materials. An EFG process is the process described in U.S. Pat. No. 4,639,218 for making a crystalline alpha-alumina rod having a cross-sectional configuration approximating that of an orthodontic bracket. The EFG process is described by LaBelle in "EFG—The Invention and Application to Sapphire Growth", in Journal or Crystal Growth, 50, pages 8–17 (September 1980). See also LaBelle, U.S. Pat. No. 3,591,348, LaBelle et al., U.S. Pat. Nos. 3,701,636 and 3,915,662, and other patents and articles cited in the Journal of Crystal Growth article. Similar techniques can be used to grow the crystalline materials for use in the orthodontic brackets of this invention.

Another technique is the Czochralski process in which a single crystal boule of the crystalline material is drawn from a melt. The boules may be sliced to provide flat stock material for fabrication.

Although the EFG technique can provide the advantage of a near net cross-sectional shape, the Czochralski technique is typically preferred to provide crystalline stock material for orthodontic brackets. There are several reasons for this preference. The Czochralki technique does not involve the use of any dies as does the EFG technique. The dies, which operate at the high temperatures of the melt, can be a source of contaminants to the crystalline stock. These contaminants can adversely affect the light transmission and/or color quality of the crystalline material. Also, the EFG technique is prone to inducing more strain within the crystal structure. Another problem which usually occurs in greater frequency with the EFG technique than the Czochralski technique is the inclusion of defects within the crystal structure such as bubbles. Moreover, the bar stock from the EFG technique generally has exterior ridges or waves caused by the interaction of the die and the melt, the surface of which freezes as it passes through the die.

Figure 1:
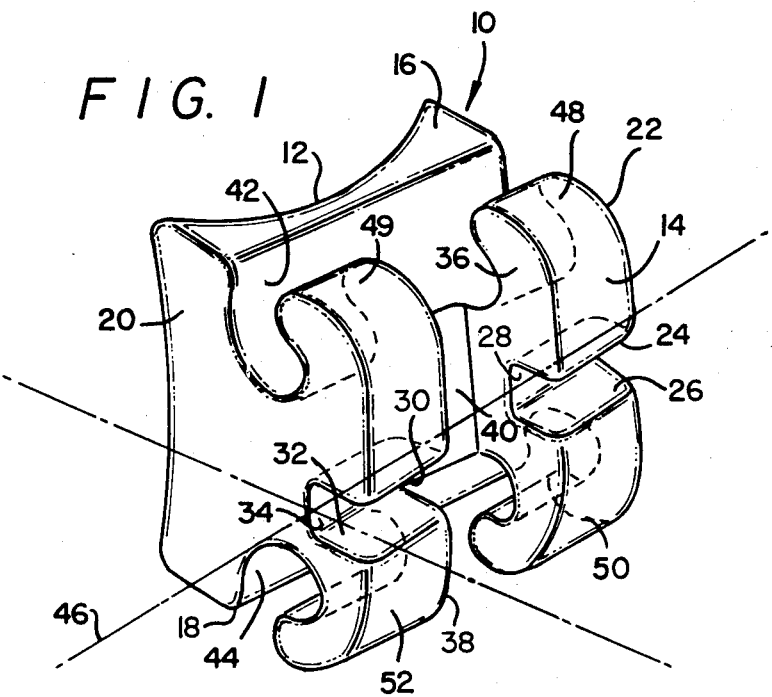
FIG. 1 is a perspective view of an orthodontic bracket made of crystalline alpha-alumina.

With reference to FIG. 1, an orthodontic bracket 10 having two pair of tie wings is fabricated completely of crystalline material. The bracket has base face 12 which is depicted as being concave to fit the curvature of the tooth. Front face 14 is that face seen when directly looking at the mouth of the patient. Front face 14 may be parallel to the plane generally defined by the base face; however, the front face and the base face are typically at an angle of up to about 15° with respect to each other to facilitate the function of the orthodontic bracket. The bracket also defines top side 16 and bottom side 18 and edges 20 and 22. As can readily be seen from the Figure, the faces and sides can be curved. For the sake of the ease of understanding, the top and bottom faces, sides and edge faces referred to herein may be described as being in a plane. The plane referenced is that most closely characteristic of the orientation of the face, side or edge to which reference is being made.

The dimensions of the bracket may vary. Usually, the width (average distance between the faces) is between about 1 and 5 millimeters, the height (average distance between the planes of the top and bottom sides) is between about 1 and 5 millimeters, and the thickness (average distance between the planes of the front and back faces) is between about 1 and 4 millimeters. The dimensions are selected from functional and aesthetic standpoints.

Figure 4:
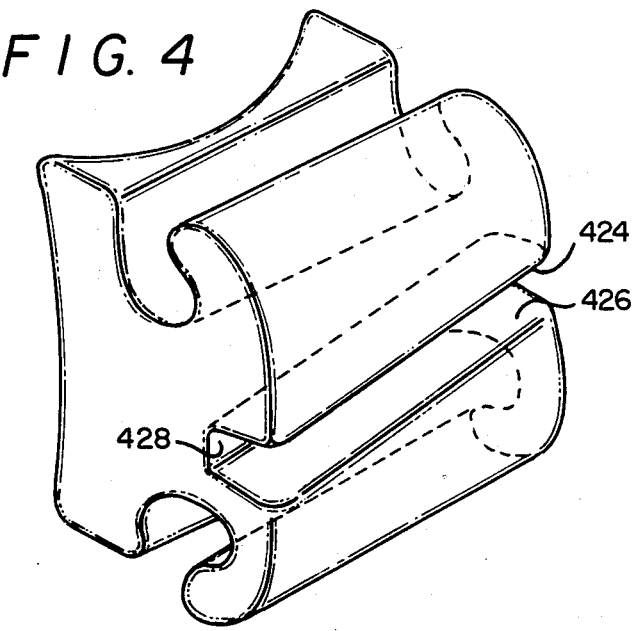
FIG. 4 is a perspective view of a "single wing" orthodontic bracket.

The front face defines an arch wire groove which extends between edge faces 20 and 22. The arch wire groove is defined by walls 24, 26, 28, 30, 32, 34, and the "saddle" defined by walls 36, 38, 40 of a double tie wing, or twin, bracket (such as is shown in FIG. 1). A single wing bracket 400 is shown in FIG. 4. In the single wing bracket 400 the archwire groove is defined by walls 424, 426 and 428 and no saddle exists. The arch wire groove may extend normal to the axis of an edge face or at an angle thereto, e.g., up to about 20°, for purposes of enhancing the function of the orthodontic bracket. The edge faces are depicted as being at right angles to the top and bottom sides; however, the edge faces and sides may form a structure having a trapazoidal cross-sectional configuration, e.g., a parallelogrammic or rhombohedric cross-section, in which case, the arch wire groove is often substantially parallel to the planes defined by the top and bottom surfaces. See, for instance, U.S. Pat. No. 4,415,330.

The arch wire groove is sized to receive the arch wire extending between teeth. Accordingly, the groove is relatively small, often about 0.4 to 0.6 (typically about 0.5) millimeter in depth. The bottom surface 34 of the arch wire groove is normally flat due to machinery considerations although curved configurations can be used. The bottom surface 28 and 34 of the arch wire groove can be equidistant from the front face or may be closer to the front face at certain regions than others. The particular design will depend upon the designer and the sought function. For the purposes of the description herein, the longitudinal axis 46 of the arch wire groove shall be the axis most closely characterized by the arch wire groove.

The top and bottom sides have surfaces 42 and 44, respectively, which define the tie wing sections 48, 49, 50 and 52 of the orthodontic bracket. As depicted in FIG. 1, surfaces 42 and 44 are indentations in the top and bottom sides. Alternatively, the tie wings may extend outwardly from the top and bottom surfaces. The tie wings are most often the portions of the orthodontic bracket to break during fabrication as well as during installation and use. The breaks may involve a cleavage between the bottom surface of the tie wing groove and the indentation defined by either surface 42 or 44, or alternatively may involve chipping of the tips of the tie wings (especially during machining).

The machining of the orthodontic bracket may be effected by any suitable technique. Often blanks are prepared and then by a series of cutting, grinding, and polishing steps the bracket is fabricated. A diamond cutting wheel can be used to cut out the archwire groove. Edges may be beveled by grinding, and corners rounded off by polishing. Subsequent annealing treatments can also be used.

The brackets are preferably polished after annealing to smooth off contours and to remove any surface imperfections which could encourage propagation of cracks. A flux polishing procedure can be used.

In the preferred aspects of this invention, certain crystal orientations are provided with respect to the bracket geometry to enhance the ability to fabricate, install and use the orthodontic bracket. As can be perceived from the foregoing discussion, the machining required to form the orthodontic bracket can be complex and involves many different forces. Breakage most often occurs during machining. Moreover, the stresses placed on the bracket during installation and use are also complex. The most severe stresses occur during installation and adjustments, but the forces that are produced during mastication can also be formidable.

In accordance with a preferred embodiment of this invention, the crystalline stock is oriented such that the axis of each plane of the cubic crystal is at an angle of between about 50° and 70°, preferably 55° and 65°, with respect to the longitudinal axis of the arch wire groove. FIG. 2 is a representation of planes in a cubic crystal. The planes form a generally cubic crystal 200 having plane 202 defined within corners 214, 216, 224 and 228; plane 204 defined within corners 214, 218, 226 and 228; plane 206 defined within corners 214, 216, 218 and 220; plane 208 defined within corners 216, 220, 222 and 224; plane 210 defined within corners 218, 220, 222 and 226; and plane 212 defined within corners 222, 224, 226 and 228. Preferably, the longitudinal axis 46 of the arch wire groove substantially intersects at least two of the following pairs of corners: 214 and 222; 216 and 226; 218 and 224; and 220 and 228. By substantially intersects, it is meant that longitudinal axis 46 is within about 10°, preferably about 5°, of the axis passing through any of the aforementioned sets of pairs of corners.

Figure 3:
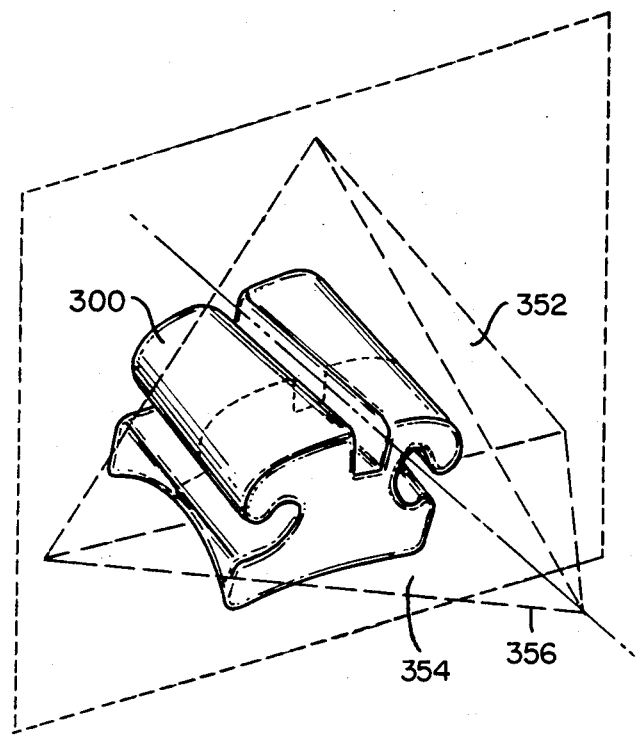
FIG. 3 is a perspective view of an orthodontic bracket depicting a preferred orientation of crystalline planes in an orthodontic bracket.

Due to the geometries of the planes, the planes substantially intersecting at the longitudinal axis 46 will pass through a plane normal to the longitudinal axis of the arch wire groove in the pattern of a triangle. This cross-sectional plane is generally depicted as plane 230 in FIG. 2 and the dotted line indicates the triangular area of intersection. FIG. 3 depicts an orthodontic bracket 300 having superimposed thereon the orientations of the planes 352, 354 and 356.

The preferred plane orientations of the present invention provide desirable resistance for cleavage of the tie wings at the arch wire groove while providing resistance to tie wing chipping. Preferably, the planes are oriented such that a corner of the cube formed by the planes is within 30°, preferably 20°, of the plane extending from the axis of the arch wire groove in a direction perpendicular to the plane of the front face of the bracket.

In alternative embodiments of the invention, the most critical load bearing portions of the bracket are made of a crystalline material, while the remainder is made of another transparent material, such as polycarbonate or polysulfone plastic, that is less expensive, easier to work, and easier to bond to the tooth.

Bonding a crystalline bracket to the tooth (or to a plastic base or to any other substrate) must be done with care. Many of the ordinary orthodontic cements (which are usually acrylic resins) will not adhere well to crystalline material without taking steps to enhance the adhesion. One means of enhancing the adhesion of a crystalline bracket to the tooth is illustrated in FIGS. 13 and 14 of U.S. Pat. No. 4,639,218 in which a bracket is shown that has an undercut or keyway in the back face of the bracket. Orthodontic cement filling the keyway will have enhanced mechanical adhesion to the bracket because of the undercut portion. The undercuts can also serve as slots for the insertion of pliers or the like for the orthodontic treatment.

Another means of enhancing the adhesion of cements such as acrylic resins to a crystalline bracket is to alter the surface of the crystalline material in such a way as to increase the strength of the adhesive bond between the crystalline material and the cement. It is known, for instance, that a wide variety of silicone coupling agents can be used to enhance the adhesive force between siliceous substrates and a wide variety of thermosetting plastics. This technology may be utilized by coating the crystalline surface that is to be in contact with the cement with a thin coating (usually thinner than about 10,000 angstroms, and preferably, up to about 1,000 angstroms) of a siliceous material such as silica, and then using silicone or silane coupling agents to enhance the bond of that surface to the cement, in a manner analogous to that which is presently known. Examples of means for coating the crystalline surface with a siliceous material are cathode sputtering, plasma deposition, and electron beam evaporation, all of which are known techniques, especially in the semiconductor arts.

The crystalline bracket having its base or tooth-contacting surface sputter coated with silica or other siliceous material such as a glass, has excellent affinity for silicone coupling agents such as A-174 (gamma-methacryloxypropyltrimethoxy silane), and by using such coupling agents the adhesion of the bracket to acrylic orthodontic cements is enhanced.

Another method for enhancing the affinity of the crystalline bracket o silicone coupling agents is to heat the brackets to remove adsorbed water, and then treat the bracket with a dilute solution (e.g., a 2 to 2.5 weight per cent solution in toluene/propylene glycol monomethyl ether) of a silane coupling agent such as A-174.

The orthodontic brackets of the invention have enhanced esthetics because of the transparency of the crystalline material.

Typical properties of the applicable crystalline materials of the present invention are set forth in the Table below.

TABLE

| MAT'L. | M.P. (°C.) | Structure | Color | Hardness | Cleavage Planes | Comments |
|---|---|---|---|---|---|---|
| $TiO_2$ | 1825 | Tetragonal | Very Pale* Yellow | 6.5 | 110 | Czochralski Growth |
| $Y_2O_3$ | 2450 | Cubic | Clear | 6.8 | | |
| MgO | 2850 | Cubic | Clear | 6.0 | 100 | |
| $SrTiO_3$ | 2080 | Cubic | Clear | 6.0 | | Czochralski Growth |

TABLE-continued

| MAT'L. | M.P. (°C.) | Structure | Color | Hardness | Cleavage Planes | Comments |
|---|---|---|---|---|---|---|
| ZrO$_2$ | ~2700 | Cubic** | Clear | 6.5 | | |
| Al$_2$O$_3$ | 2040 | Rhombohedral | Clear | 9.0 | 1T02 | Czochralski Growth |

*After O$_2$ Anneal
**Stabilized with Y$_2$O$_3$

A particularly useful test for evaluating orthodontic brackets is to insert a flat blade into the arch wire groove and twist the blade around an axis perpendicular to the longitudinal axis of the arch wire groove. The greater the force required to fracture the bracket, the better the crystal orientation within the bracket.

It is claimed:

1. An orthodontic bracket comprising a body comprising crystalline material having crystalline planes of the group consisting of zirconia, yttria, magnesia and strontium titanate having a base face intended to face a tooth and an opposing front face defining a longitudinal arch wire groove.

2. The orthodontic bracket of claim 1 wherein said bracket is made entirely of crystalline zirconia.

3. The orthodontic bracket of claim 1 wherein said bracket is made entirely of crystalline yttria.

4. The orthodontic bracket of claim 1 in which the axis of each plane of the crystalline material is at an angle of between about 50° and 70° with respect to the longitudinal axis of the arch wire groove.

5. The orthodontic bracket of claim 3 wherein said material is zirconia.

6. The orthodontic bracket of claim 1 having at least one pair of tie wings.

7. The orthodontic bracket of claim 1 wherein said bracket has a rhomboidal configuration when viewed looking directly at the front of the bracket.

8. The orthodontic bracket of claim 1 wherein the archwire groove is oriented essentially parallel to the top and bottom faces of the bracket.

9. The orthodontic bracket of claim 1 in which the crystalline material is cubic and wherein three planes of said cubic crystalline material intersect substantially at an axis parallel to the longitudinal axis of the arch wire groove.

* * * * *